United States Patent
Atienza et al.

(10) Patent No.: US 9,890,182 B2
(45) Date of Patent: *Feb. 13, 2018

(54) SELECTIVE 1,2-HYDROSILYLATION OF TERMINALLY UNSATURATED 1,3-DIENES USING IRON CATALYSTS

(71) Applicants: MOMENTIVE PERFORMANCE MATERIALS INC., Waterford, NY (US); PRINCETON UNIVERSITY, Princeton, NJ (US)

(72) Inventors: Crisita Carmen Hojilla Atienza, Houston, TX (US); Aroop Kumar Roy, Mechanicville, NY (US); Paul J. Chirik, Princeton, NJ (US); Keith J. Weller, Rensselaer, NY (US); Johannes G. P. Delis, Bergen op Zoom (NL); Tianning Diao, Plainsboro, NJ (US)

(73) Assignees: MOMENTIVE PERFORMANCE MATERIALS INC., Waterford, NY (US); PRINCETON UNIVERSITY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,661

(22) Filed: May 6, 2014

(65) Prior Publication Data

US 2014/0330024 A1 Nov. 6, 2014

Related U.S. Application Data

(60) Provisional application No. 61/819,726, filed on May 6, 2013.

(51) Int. Cl.
  *C07F 7/08* (2006.01)
  *B01J 31/18* (2006.01)

(52) U.S. Cl.
  CPC ......... *C07F 7/0812* (2013.01); *B01J 31/1815* (2013.01); *C07F 7/0803* (2013.01); *B01J 2231/323* (2013.01); *B01J 2531/0216* (2013.01); *B01J 2531/0244* (2013.01); *B01J 2531/842* (2013.01)

(58) Field of Classification Search
  CPC .... C07F 7/0812; C07F 7/0803; B01J 31/1815
  See application file for complete search history.

(56) References Cited

U.S. PATENT DOCUMENTS

| | | | |
|---|---|---|---|
| 3,159,601 A | 12/1964 | Ashby et al. | |
| 3,220,972 A | 11/1965 | Lamoreaux | |
| 3,296,291 A | 1/1967 | Chalk et al. | |
| 3,775,452 A | 11/1973 | Karstedt | |
| 3,928,629 A | 12/1975 | Chandra et al. | |
| 4,550,152 A | 10/1985 | Faltynek | |
| 4,572,791 A | 2/1986 | Onopchenko et al. | |
| 4,578,497 A | 3/1986 | Onopchenko et al. | |
| 4,729,821 A | 3/1988 | Timmons et al. | |
| 4,788,312 A | 11/1988 | Paciorek et al. | |
| 5,026,893 A | 6/1991 | Paciorek | |
| 5,166,298 A | 11/1992 | Friedman et al. | |
| 5,247,045 A * | 9/1993 | Durfee ................. | C08G 77/385 528/15 |
| 5,331,075 A | 7/1994 | Sumpter et al. | |
| 5,432,140 A | 7/1995 | Sumpter et al. | |
| 5,866,663 A | 2/1999 | Brookhart et al. | |
| 5,955,555 A | 9/1999 | Bennett | |
| 6,060,620 A * | 5/2000 | Tachikawa ............ | C07F 7/1896 549/215 |
| 6,103,946 A | 8/2000 | Brookhart et al. | |
| 6,214,761 B1 | 4/2001 | Bennett | |
| 6,265,497 B1 | 7/2001 | Herzig | |
| 6,278,011 B1 | 8/2001 | Chen et al. | |
| 6,281,303 B1 | 10/2001 | Lavoie et al. | |
| 6,297,338 B1 | 10/2001 | Cotts et al. | |
| 6,417,305 B2 | 7/2002 | Bennett | |
| 6,423,848 B2 | 7/2002 | Bennett | |
| 6,432,862 B1 | 8/2002 | Bennett | |
| 6,451,939 B1 | 9/2002 | Britovsek | |
| 6,455,660 B1 | 9/2002 | Clutton et al. | |
| 6,458,739 B1 | 10/2002 | Kimberley et al. | |
| 6,458,905 B1 | 10/2002 | Schmidt et al. | |
| 6,461,994 B1 | 10/2002 | Gibson et al. | |
| 6,472,341 B1 | 10/2002 | Kimberley et al. | |

(Continued)

FOREIGN PATENT DOCUMENTS

| | | |
|---|---|---|
| CN | 1727349 | 2/2006 |
| EP | 0786463 | 7/1997 |

(Continued)

OTHER PUBLICATIONS

International Search Report and the Written Opinion of the International Searching Authority, PCT/US2014/036925, Momentive Performance Materials Inc., Dec. 19, 2014.
Tondreau, Aaron M. et al., Iron Catalysts for Selective Anti-Markovnikov Alkene Hydrosilylation Using Tertiary Silanes, Science, vol. 335, Feb. 3, 2012, pp. 566-570.
Wu, Jessica Y., A Strategy for the Synthesis of Well-Defined Iron Catalysts and Application to Regioselective Diene Hydrosilylation, J. Am. Chem. Soc. 2010, 132, 13214-13216.
Cornish, Andrew J. et al., Homogeneous Catalysis, Journal of Organometallic Chemistry, 172 (1979) pp. 153-163.
Woo et al., "Redistribution of Bos- and Tris(silyl)methanes Catalyzed by Red-Al," Bull. Korean. Chem. Soc. 1996, 17, 123-125.

(Continued)

*Primary Examiner* — Joseph R Kosack
(74) *Attorney, Agent, or Firm* — Joseph Waters; McDonalds Hopkins LLC

(57) ABSTRACT

The present invention is directed to a selective and efficient process for the hydrosilylation of compounds containing terminally unsaturated 1,3-dienes using iron-based hydrosilylation catalysts. The resulting 1,2-addition products are useful as precursors for various silicone materials or silane- or silyl/silicone-functionalized polyolefins.

19 Claims, No Drawings

(56) References Cited

U.S. PATENT DOCUMENTS

| | | |
|---|---|---|
| 6,620,895 B1 | 9/2003 | Coils et al. |
| 6,657,026 B1 | 12/2003 | Kimberley et al. |
| 7,053,020 B2 | 5/2006 | DeBoer et al. |
| 7,148,304 B2 | 12/2006 | Kimberley et al. |
| 7,161,005 B2 | 1/2007 | Schlingloff et al. |
| 7,247,687 B2 | 7/2007 | Cherkasov et al. |
| 7,268,096 B2 | 9/2007 | Small et al. |
| 7,429,672 B2 | 9/2008 | Lewis et al. |
| 7,442,819 B2 | 10/2008 | Ionkin et al. |
| 7,456,285 B2 | 11/2008 | Schlingloff et al. |
| 7,696,269 B2 | 4/2010 | Cruse et al. |
| 8,236,915 B2 | 8/2012 | Delis et al. |
| 8,415,443 B2 | 4/2013 | Delis et al. |
| 2002/0058584 A1 | 5/2002 | Bennett |
| 2006/0263675 A1 | 11/2006 | Adzic et al. |
| 2007/0264189 A1 | 11/2007 | Adzic et al. |
| 2008/0262225 A1 | 11/2008 | Schlingloff et al. |
| 2008/0293878 A1 | 11/2008 | Funk et al. |
| 2009/0068282 A1 | 3/2009 | Schlingloff et al. |
| 2009/0296195 A1 | 12/2009 | Fontana et al. |
| 2011/0009565 A1 | 1/2011 | Delis et al. |
| 2011/0009573 A1* | 1/2011 | Delis .................. C07F 15/02 525/453 |
| 2012/0130021 A1 | 5/2012 | Tondreau et al. |
| 2012/0130105 A1 | 5/2012 | Lewis et al. |
| 2012/0130106 A1 | 5/2012 | Lewis et al. |
| 2013/0158281 A1* | 6/2013 | Weller ................ B01J 31/1805 556/425 |
| 2014/0051822 A1 | 2/2014 | Atienza et al. |
| 2014/0243486 A1 | 8/2014 | Roy et al. |
| 2014/0330024 A1 | 11/2014 | Atienza et al. |
| 2014/0330036 A1 | 11/2014 | Lewis et al. |
| 2014/0343311 A1 | 11/2014 | Boyer et al. |
| 2015/0080536 A1 | 3/2015 | Diao et al. |
| 2015/0137033 A1 | 5/2015 | Diao et al. |

FOREIGN PATENT DOCUMENTS

| | | | |
|---|---|---|---|
| GB | 2013207 | 8/1979 | |
| GB | 2013207 A * | 8/1979 | ............ C07F 7/00 |
| TW | 200902541 | 1/2009 | |
| WO | 9210544 | 6/1992 | |
| WO | 2002088289 | 11/2002 | |
| WO | 2003042131 | 5/2003 | |
| WO | 2008085453 | 7/2008 | |
| WO | 2011006044 | 1/2011 | |
| WO | 2012/007139 | 1/2012 | |
| WO | 2012071359 | 5/2012 | |
| WO | 2013/043783 | 3/2013 | |
| WO | 2013043846 | 3/2013 | |

OTHER PUBLICATIONS

Wu et al., "A Strategy for the Synthesis of Well-Defined Iron Catalysts and Application to Regioselective Diene Hydrosilylation," Journal of the American Chemical Society, vol. 132, No. 38. Sep. 29, 2010 (Sep. 29, 2010), pp. 13214-13216.

Yi, Chae S. et al., "Regioselective Intermolecular Coupling Reaction of Arylketones and Alkenes Involving C—H Bond Activation Catalyzed by an in Situ Formed Cationic Ruthenium Hydride Complex," Organometallics, vol. 28, pp. 4266-4268 (2009).

Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).

Speier et al., "The Addition of Silicon Hydridesto Olefinic Double Donds. Part II. The Use of Group VII Metal Catalysts," J. Am. Chem. Soc. 1957, vol. 79, 974.

Kamata et al. "Catalytic Hydrosilylation of Alkenes by Iron Complexes Containing Terpyridine Derivatives as Ancillary Ligands," Organometallics, 2012, vol. 31, pp. 3825-3828.

Kaverin et al., "Reaction of Polar Olefins with Methyldichlorosilane on nickel-containing Catalytic Systems," Chemical Abstracts Service, 1980, vol. 92, p. 622.

Benkeser et al., "Chloroplatinic acid catalyzed additions of silanes to isoprene," J. Organoment. Chem.1978,156, pp. 235-244.

Schmidt et al., "Heterogenized Iron (II) Complexes as Highly Active Ethene Polymerization Cayalysts," Journal of Molecular Catalysis A: Chemical, 2002, vol. 179, pp. 155-173.

Shaikh et al., "A convenient and General Iron-Catalyzed Hydrosilylation of Aldehydes," Organic Letters 2007, vol. 9, No. 26, pp. 5429-5432.

Small et al., "Highly Active Iron and Cobalt Catalysts for the Polymerization of Ethylene," J.Am. Chem. Soc. 1998, 120 (16), pp. 4049-40450.

Toma et al., J. Braz. Chem. Soc., vol. 7, No. 6, 391-394, 1996.

Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.

Ittel et al., DuPont's Versipol®Late Metal Polymerization Catalysts, http://www.nacatsoc.org/18nam/Orals/044-Ittel-DuPont's %20Versipol%C2%AE%20Late%20Metal%20Polymerization.pdf.

Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.

Oro et al. "Hydrosilylation of Alkenese by Iridium Complexes," J. Mol. Catalysis, 1986, 37, 151-156.

Naumov et al., "Selective Dehydrogentative Silylation-Hydrogenation Reaction of Divinyldisiloxane with Hydrosilane Catalyzed by an Iron Complex," Journal of the American Chemical Society, 2012, vol. 134, Issue 2, 804-807, Osaka, Japan.

McAtee et al., "Preparation of Allyl and Vinyl Silanes by the Palladium-Catalyzed Silylation of Terminal Olefins: A Silyl-Heck Reaction"", Angewandte Chemie, Int. Ed. 2012, 51, 3663-3667.

Marciniec et al., "Competitve silylation of olefins with vinylsilanes and hydrosilanes photocatalyzed by iron carbonyl complexes," Inorg. Chem. Commun. 2000, 3, 371.

Lu et al., "Iridium-Catalyzed (Z)-Trialkylsilylation ofTerminal Olefins," J. Org. Chem, 2010, 75, 1701-1705, Dallas, Texas.

Kuo, et al., "Electrochemical studies of nickel bis(2,2':6',2"-terpyridine) with alkyl/aryl/allyl bromides and activeated olefins in nonaqueous solvents" Jiemian Kexue Huishi, vol. 15, Issue 1, pp. 23-42, Journal, 1992, Coden: CMKCEW, ISSN: 1026-325X.

Kakiuchi et al., "Dehydrogenative Silylation of 1,5-Dienes with Hydrosilanes Catalyzed by RhCl (PPh3)3," Am. Chem. Soc., Organometallics, 1993, 12, 4748-4750, Kagawa, Japan.

Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.

Humphries et al., "Investigations into the Mechanism of Activation and Initiation of Ethylene Polymerization by Bis(imino)pyridine Cobalt Catalysts: Synthesis, Structures, and Deuterium Labeling Studies," Organometallics 2005, 24, 2039-2050, London, United Kingdom.

Fernandez et al., "Synthesis and Reactions of Dihydrido(triethylalyl)(1,5-cycloctadiene)-Iridium(III) Complexes: Catalysts for Dehydrogneative Silylation of Alkenese," Organometallics, 1986, 5, 1519-1520.

Chen et al., "General Synthesis of Di-u-oxo Dimanganese Complexes as Functional Models for the Oxygen Evolving Complex of Photosystem II" Inorg. Chem. 2005, 44, 7661-7670.

Bowman et al., "Synthesis and Molecular and Electronic Structures of Reduced Bis(imino) pyridine Cobalt Dinitrogen Complexes: Ligand versus Metal Reduction," J. Am. Chem. Soc., 2010, 132, 1676-1684, Germany.

Anselment et al., "Activation of Late Transition Metal Catalysts for Olefin Polymerizations and Olefin/CO Copolymeriations," Dalton Transactions, vol. 34, pp. 4525-4672.

Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2012.

Atienza, "Reactivity of Bis(Imino)Pyridine Cobalt Complexes in C—H Bond Activation and Catalytic C—C and C—Si Bond Formation" PhD thesis, Jun. 2013, Princeton University.

(56) References Cited

OTHER PUBLICATIONS

Shaikh et al., "Iron-Catalyzed Enantioselevtive Hydrosilylation of Keytones," Angew. Chem. Int. Ed., 2008, 47, 2497-2501.
De Bo et al., "Hydrosilylation of Alkynes Mediated by N-heterocyclic Carben Platinum(0) Complexes," Organometallics, 2006, 25, 1881-1890.
Boudjouk et al., "Exclusive β-hydrosilylation of acrylates catalysed by copper-tetramethylethylenediamine ," Journal of Organometallic Chemistry, Jan. 1, 1993, pp. 41-43.
Brookhart et al., "Mechanism of a cobalt(III)-catalyzed olefin hydrosilation reaction: direct evidence for a silyl migration pathway," J. Am. Chem. Soc. 1993, 115, 2151.
Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).
Cornish, et al., "Homogeneous catalysis: VI. Hydrosilylation using tri(pentanedionato)rhodium(III) or tetrakis(μ-acetato) Dirhodium(II) as Catalysts," Journal of Organometallic Chemistry, Elsevier-Sequoia S.A. Lausanne, CH, vol. 172, No. 2, Jun. 12, 1979 (Jun. 12, 1979), pp. 153-163.
Chuit et al. "Reactivity of penta- and hexacoordinate silicon compounds and their role as reaction intermediates," Chem. Rev. 1993, 93, 1371-1448.
De Rycke et al., "Toward reactant encapsulation for substrate-selectivity," Tetrahedron Lett. 2012, 53, 462.
Doucette, "Homogeneous Iron Catalysts With Redox-Active Ligands: Synthesis and Electronic Structure," Dissertation Cornell University, Aug. 2006.
Doyle et al., "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.
Falck, J. R. et al. "Iridium-Catalyzed (Z)-Trialkylsilylation of Terminal Olefins," J. Org. Chem. 2010, 75, 1701.
Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.
Gandon, et al., "Silicon-Hydrogen Bond Activation and Hydrosilylation of Alkenes Mediated by CpCo Complexes: A Theoretical Study," J. Am. Chem. Soc. 2009, 131, 3007.
Hori et al., "Ruthenium Complex-Catalyzed Silylation of Olefins. Selective Sysnthesis of Allysilanes," Bull. Chem. Soc. Jpn., 1988, 61, 3011-3013, Kyoto, Japan.
Itoh et al., "Disproportionation reactions of organohydrosilanes in the presence of base catalysts" J. Organomet. Chem., 2001, 629, 1-6.
Ivchenko et al., "A convenient approach for the synthesis of 2,6-diformyl- and 2,6-diacetylpyridines," Tetrahedron Lett. 2013, 54, 217.
Fruchtel et al; "Organic Chemistry on Solid Supports," Angewandte Chemie International Edition in English, 1996, vol. 35, Issue 1, pates 17-42.
Junge et al., "Iron-Catalyzed Reduction of Carboxylic Esters to Alcohols," European Journal of Organic Chemistry, vol. 2013, No. 11, Mar. 1, 2013, pp. 2016-2065.
Knijnenburg et al., "Olefin hydrogenation using diimine pyridine complexes of Co and Rh," Journal of Molecular Catalysis, 232 (2005), No. 1-2, pp. 151-159.
Marciniec, Bogdan, "Catalysis by Transition Metal Complexes of Alkene Silylation—Recent Progress and Mechanistic Implications," Coordination Chemistry Reviews, 249 (2009) 2374-2390.
Marciniec et al. "Encyclopedia of Catalysis" pp. 6,7, and 20, Mar. 5, 2010.
Martinez, Remi et al., "C—C Bond Formation via C—H Bond Activation Using an in Situ-Generated Ruthenium Catalyst," Journal of the American Chemical Society, vol. 131, pp. 7887-7895 (2009).

McAtee et al., "Rational Design of a Second Generation Catalyst for Preparation of Allylsilanes Using the Silyl-Heck Reaction," J. Am. Chem. Soc. 2014, 136 (28), 10166-10172.
Bareille et al., "First Titanium-Catalyzed anti-1,4-Hydrosilylation of Dienes," Organometallics, 2005, 24(24), 5802-5806.
Nishiyama et al., "An Iron-Catalysed Hydrosilylation of Ketones," Chem. Commun., Royal Society of Chemistry, 2007, 760-762.
Furuta et al., "Highly efficient catalytic system for hydrosilylation of ketones with iron(II) acetate-thiophenecarboxylate," Tetrahedron Letters, 2008, vol. 49, Issue 1, pp. 110-113.
Ojima et al., "Regioselective hydrosilylation of 1,3-dienes catalyzed by phosphine complexes of palladium and rhodium," J. Organomet. Chem. 1978, 157, 359-372.
Pettigrew, "Synthetic Lubricants and High Performance Fluids, Ch. 12 Silahydrcarbons" (second edition), L. R. Rudnick and L R. Shubkin (Editors), Marcel Dekker, NY 1999, pp. 287-296.
Poyatos, Macarena et al., "Coordination Chemistry of a Modular N,C-Chelating Oxazole-Carbene Ligand and Its Applications in Hydrosilylation Catalysis," Organometallics, vol. 25, pp. 2634-2641 (2006).
Reiff, W. M. et al., "Mono(2,2',2"-terpyridine) Complexes of Iron(II)," Journal of Inorganic Chemistry, vol. 8, No. 9, pp. 2019-2021 (1969).
Parker et al. "1,2-Selective Hydrosilylation of Conjugated Dienes," J. Am. Chem. Soc., 2014, 136 (13), pp. 4857-4860.
Archer et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).
Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.
Zhu et al., "A Measure for *-Donor and *-Acceptor Properties of Diiminepyridine-Type Ligands," Organometallics 2008, 27, 2699-2705.
Zhu et al., "(Py)2Co(CH2SiMe3)2 As an Easily Accessible Source of "CoR2"," Organometallics, 2010, 29 (8), 1897-1908.
Yeung, et al., "Cobalt and iron complexes of chiral C1- and C2-terpyridines: Synthesis, characterizationa dn use in catalytic asymmetric cyclopropanation of styrenes." Inorganica Chimica Acta 362 (2009) 3267-3273.
Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.
Bart et al., "Preparation and Molecular and Electronic Structures of Iron(0) Dinitrogen and Silane 6Complexes and Their Application to Catalytic Hydrogenation and Hydrosilation," Journal of the American Chemical Society, vol. 126, pp. 13794-13807 (2004).
Connelly et al., "Chemical Redox Agents for Organometallic Chemistry," Chem. Rev. 1996, 96, 877-910.
Atienza et al. "Synthesis, Electronic Structure, and Ethylene Polymerization Activity of Bis(imino)pyridine Cobalt Alkyl Cations," Agnewandte Chem. Int. Ed. 2011, 50, 8143-8147.
Glatz et al., "Terpyridine-Based Silica Supports Prepared by Ring-Opening Metathesis Polymerization for the Selective Extraction of Noble Metals," Journal of Chromatography A, vol. 1015, pp. 65-71 (2003).
Nagashima et al., "Dehydrogenative Silylation of Ketones with a Bifunctional Organosilane by Rhodium-Pybox Catalysts," Chem. Soc. of Jpn., Chemistry Letters, 1993, 347-350, Toyohashi, Aichi 441.
Hosokawa et al., "A Chiral Iron Complex Containing a Bis(oxazolinyl)phenyl Ligand: Preparation and Asymmetric Hydrosilylation of Ketones," Organometallics, 29, 5773-5775 (2010).
Kaul et al., "Immobilization of Bis(imino)pyridyliron (II) complexes on Silica," Organometallics, 2002, 21(1), 74-83.
Kim et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).

(56) References Cited

OTHER PUBLICATIONS

Kroll et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).
Field et al., "One-Pot Tandem Hydroamination/Hydrosilation Catalyzed by Cationic Iridium(I) Complexes," Organometallics, vol. 22, pp. 4393-4395, Sep. 25, 2003.
Dekamin et al., "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.
Nesmeyanov et al., "Addition, Substitution, and Telomerization Reactions of Olefins in the Presence of Metal Carbonyls or Colloidal Iron," Tetrahedron, vol. 17, pp. 61-68 (1962).
Pal, et al., "Preparation and hydrosilylation activity of a molybdenum carbonyl complex that features a pentadentate bis(amino)pyridine lignad," Inorg Chem. Sep. 2, 2014; 53(17):9357-65. doi: 10.1021/ic501465v. Epub Aug. 20, 2014.
Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.
Buschbeck et al., "Triethylene Glycol Ether End-grafted Carbosilane Dendrimers: Synthesis and Complexation Behavior," Inorganic Chemistry Communications, vol. 7, pp. 1213-1216, Oct. 13, 2004.
Seckin, "Preparation and Catalytic Properties of a Ru(II) Coordinated Polyimide Supported by a Ligand Containing Terpyridine Units," Journal of Inorganic and Organometallic Polymers and Materials, Apr. 9, 2009, 19(2), 143-151.
Sieh et al., "Metal-Ligand Electron Transfer in 4d and 5d Group 9 Transition Metal Complexes with Pyridine, Diimine Ligands," Eur. J. Inorg. Chem., 2012:444-462. doi 10.1002/ejic.201101072.
Speier et al., "The Addition of Silicon Hydrides to Olefinic Double Bonds. Part II. The Use of Group VIII Metal Catalysts," Journal of the American Chemical Society, vol. 79, pp. 974-979 (1956).
Thammavongsy et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.
Timpa, "Non-Innocent Pyridine Based Pincer Ligands and Their Role Catalysis" Nov. 1, 2010.
Tondreau, et al., "Enantiopure Pyridine Bis(oxazoline) "Pybox" and Bis(oxazoline) "Box" iron Dialkyl Complexes: Comparison to Bis(imino)pyridine Compounds and Application to Catalytic Hydrosilylation of Ketones," Organometallics, Jun. 9, 2009, 28(13), 3928-3940.
Tondreau, et al "Synthesis and electronic structure of cationic, neutral, and anionic bis (imino)pyridine iron alkyl complexes: evaluation of redox activity in single-component ethylene polymerization catalysts." J Am Chem Soc. Oct. 27, 2010; 132(42): 15046-59. doi: 10.1021/ja106575b.
Gibson et al., "The nature of the active species in bis(imino)pyridyl cobalt ethylene polymerisation catalysts," Chem. Commun., 2001, 2252-2253.
Wile, et al. "Reduction chemistry of aryl- and alkyl-substituted bis(imino)pyridine iron dihalide compounds: molecular and electronic structures of [(PDI)2Fe] derivatives." Inorg Chem May 4, 2009; 48(9):4190-200.
Tondreau, et al., "Iron Catalysts for Selective Anti-Markovnikov Alkene Hydrosilylation Using Tertiary Silanes," Science, vol. 335, No. 6068, Feb. 2, 2012 (Feb. 2, 2012). pp. 567-570.
Abu-Surrah et al., "New bis(imino)pyridine-iron(II)- and cobalt(II)-based catalysts: synthesis, characterization and activity towards polymerization of ethylene" Journal of Organometallic Chemistry 648 (2002) 55-61.
Albon et al., "Metal Carbonyl Complexes Involving 2,6Bix[I-(phenylimino)ethyl]pyridine; Bidentate Corrdination of a Potentially Tridentate Ligand" Inorganica Chimica Acta, 159 (1989) 19-22.
Alyea et al., "Terdentate NNN Donor Ligands Derived from 2,6-Diacetylpyridine" Syn. React. Inorg. Metal-Org. Chem., 4(6), 535-544 (1974).
Bouwkamp, "Iron-Catalyzed [2π+2π] Cycloaddition of α,ω-Dienes the Importance of Redox-Active Supporting Ligands" Journal of the American Chemical Society, 2006, V128 N41, p. 13340-13341.
Britovsek et al., "Novel Olefin Polymerization Catalysts Based on Iron and Cobalt," Chem. Commun., 1998, 849-850.
Cetinkaya et al., "Ruthenium(ii) complexes with 2,6-pyridyl-diimine ligands: synthesis, characterization and catalytic activity in epoxidation reactions" Journal of Molecular Catalysis A: Chemical 142 (1999) 101-112.
Corey et al., "Reactions of Hydrosilanes with Transition-Metal Complexes: Formation of Stable Transition-Metal Silyl Compounds," Journal of Chemical Reviews, vol. 99, pp. 175-292 (1999).
Haarman et al., "Reactions of [RhCl(diene)]2 with Bi- and Terdentate Nitrogen Ligands. X-ray Structures of Five-Coordinate Complexes," Am. Chem. Soc., Organometallics 1997, 16, 54-67.
Kickelbick et al., New J. Chem., 2002, 26, 462-468.
Kooistra et al., Inorganica Chimica Acta 357 (2004) 2945-2952.
Lapointe, et al., "Mechanistic Studies of Palladium(II)-Catalyzed Hydrosiliation and Dehydrogenative Silation Reactions," J. Amer. Chem. Soc. 119 (1997), pp. 906-917.
Lewis et al., "Hydrosilylation Catalyzed by Metal Colloids: A Relative Activity Study," Organometallics, 9 (1990), 621-625.
Lions et al., J. Chem. Soc. (A) 1957, vol. 79, 2733-2738.
Lu et al., "The Molecular Structure of a Complex of a 2,6-Diimino-Pyridine as a Bidentate Liandd with Molybdenum Carbonyl" Inorganica Chimica Acta, 134 (1987) 229-232.
Pangborn et al., "Safe and Convenient Procedure for Solvent Purification," Oraganometallics, 15:1518 (1996).
Randolph, Claudia L. et al., "Photochemical Reactions of (η5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of the American Chemical Society, vol. 108, pp. 3366-3374 (1986).
Russell et al., "Synthesis of Aryl-Substituted Bis(imino)pyridine Iron Dinitrogen Complexes," Inorg. Chem. 2010, 49, 2782-2792.
Sacconi et al., "High-spin Five-Co-Ordinate Nickel (II) and Cobald (II) Complexes with 2,6-Diacetylepyridinebis(imines)," J. Chem. Soc. (A), 1968, 1510-1515.
Tondreau et al., "Bis(imino)pyridine Iron Complexes for Aldehyde and Ketone Hydrosilylation," Am. Chem. Soc., 2008, vol. 10, No. 13, 2789-2792.
Russell, et al., "Synthesis of Aryl-Substituted Bis(imino)pyridine Iron Dinitrogen Complexes," Inorganic Chemistry, vol. 49, No. 6, pp. 2782-2792. (2010).
Tondreau, et al., "Iron Catalysts for Selective Anti-Markovnikov Alkene Hydrosilylation Using Tertiary Silanes," Science, vol. 335, pp. 567-570. (2012).
Ojima, "The Hydrosilylation of Conjugated Dienes and Related Compounds," The Chemistry of Organic Silicon Compounds, vol. 2, pp. 1493-1499. John Wiley & Sons Ltd., (1989).
Trovitch, et al., "Carbon-Oxygen Bond Cleavage by Bis(imino)pyridine Iron Compounds: Catalyst Deactivation Pathways and Observation of Acyl C—O Bond Cleavage in Esters," Organometallics, vol. 27, No. 23, pp. 6264-6278. (2008).
Zhu, et al., "Radical Mechanisms in the Reaction of Organic Halides with Diiminepyridine Cobalt Complexes," Organometallics, vol. 31, pp. 3958-3971. (2012).

* cited by examiner

SELECTIVE 1,2-HYDROSILYLATION OF TERMINALLY UNSATURATED 1,3-DIENES USING IRON CATALYSTS

CROSS REFERENCE TO RELATED APPLICATIONS

The present application claims priority to and the benefit of U.S. Provisional Application No. 61/819,726 filed on May 6, 2013, the disclosure of which is incorporated herein by reference in its entirety.

FIELD OF THE INVENTION

This invention relates generally to processes for the hydrosilylation of diene compounds using iron-containing catalysts, and more specifically to hydrosilylation of terminally unsaturated 1,3-diene compounds using iron-containing pyridine diimine catalysts to form 1,2-addition products.

BACKGROUND OF THE INVENTION

Hydrosilylation chemistry, involving the reaction between a silyl hydride and an unsaturated organic group, is the basis for synthetic routes to produce commercial silicone products such as silicone surfactants, silicone fluids and silanes as well as many addition cured products including sealants, adhesives, and silicone-based coatings. Heretofore, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal complexes are widely accepted as catalysts for hydrosilylation reactions, they have several disadvantages. One disadvantage is that the precious metal complex catalysts are inefficient in catalyzing certain reactions. For example, in the case of hydrosilylation of allyl polyethers with silicone hydrides using precious metal complex catalysts, use of an excess amount of allyl polyether, relative to the amount of silicone hydride, is needed to compensate for the less-than-ideal selectivity of the catalyst in order to ensure complete conversion of the silicone hydride to a useful product. The excess polyether which is mostly isomerized, is also most often impractical to remove and remains in the product, and may result in undesirable color and odor in end applications.

While the above-mentioned precious metal catalysts, particularly those based on platinum, are widely used in the industry for their high activity and ease of preparation and handling, these catalysts also suffer significantly from poor selectivity towards the desired adducts, especially for olefins containing hetero-atoms such as oxygen and nitrogen close to the C=C unsaturation as well as certain multiply unsaturated substrates. Examples of the latter are terminally unsaturated dienes such as butadiene, isoprene and others, where the desirable product is a 1,2-adduct that leaves a second terminal unsaturation for convenient further derivatization and application chemistries. Historically, catalysts for hydrosilylation of 1,3-dienes produce essentially the 1,4-adducts or a mixture of 1,4- and 1,2-adducts at best where the internally unsaturated 1,4-adduct predominates or the overall reaction is inefficient. Ritter has reported Fe catalysts that selectively hydrosilylate conjugated dienes such as myrcene to form the 1,4-addition product (Ritter, T. et al J. Am. Chem. Soc. 2010, 132, 13214). Palladium and Rh catalysts (Wilkinson's catalyst) are known to hydrosilylate isoprene and myrcene to give the 1,4-addition product (I. Ojima and M. Kumagai J. Organomet. Chem. 1978, 157, 359-372).

Rhodium(III) acetylacetonate is known to hydrosilylate isoprene to give the 1,4-addition product (M. Lappert et al, J. Organomet. Chem. 1979, 172, 153-163). $Cp_2TiF_2$ is known to hydrosilylate isoprene to give the 1,4-addition product (C. Moise et al; Organometallics 2005, 5802-5806). $H_2PtCl_6$ is known to hydrosilylate isoprene to give a mixture of products (R. Roche J. Organomet. Chem. 1978, 156, 235-244). While many non-precious metals have also been investigated for 1,3-diene hydrosilylation, essentially all are known to provide either mixtures of the 1,2- and 1,4-adducts or are inefficient in producing the 1,2-adduct (B. Marciniec., Ed. Comprehensive Handbook on Hydrosilylation; Pergamon Press, 1992). Recently, Ritter, et al. reported highly selective 1,2-hydrosilylation of butadiene and other terminally unsaturated 1,3-dienes using a cyclometalated platinum complex containing a phosphine ligand (Ritter, et al. J. Am. Chem. Soc., 2014, 136 (13), pp 4857-4860.)

In addition to the less-than-desirable selectivities or regioselectivities, due to the high price of precious metals, the precious metal-containing catalysts can constitute a significant proportion of the cost of silicone formulations. Recently, global demand for precious metals, including platinum, has increased, driving prices for platinum to record highs, creating a need for effective, low cost replacement catalysts.

As an alternative to precious metals, recently, certain iron complexes have gained attention for use as hydrosilylation catalysts. Illustratively, technical journal articles have disclosed that that $Fe(CO)_5$ catalyzes hydrosilylation reactions at high temperatures. (Nesmeyanov, A. N. et al., Tetrahedron 1962, 17, 61), (Corey, J. Y et al., J. Chem. Rev. 1999, 99, 175), (C. Randolph, M. S. Wrighton, J. Am. Chem. Soc. 108 (1986) 3366). However, unwanted by-products such as the unsaturated silylolefins, which result from dehydrogenative silylation, were formed as well.

A five-coordinate Fe complex containing a pyridine diimine (PDI) ligand with isopropyl substitution at the ortho positions of the aniline rings has been used to hydrosilylate an unsaturated hydrocarbon (1-hexene) with primary and secondary silanes such as $PhSiH_3$ or $Ph_2SiH_2$ (Bart et al., J. Am. Chem. Soc., 2004, 126, 13794) (Archer, A. M. et al. Organometallics 2006, 25, 4269). However, one of the limitations of these catalysts is that they are only effective with the aforementioned primary and secondary phenyl-substituted silanes, and not with, for example, tertiary or alkyl-substituted silanes such as $Et_3SiH$, or with alkoxy substituted silanes such as $(EtO)_3SiH$.

Other Fe-PDI complexes have also been disclosed. U.S. Pat. No. 5,955,555 discloses the synthesis of certain iron or cobalt PDI dianion complexes. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053, 020 discloses a catalyst system containing, inter alia, one or more bisarylimino pyridine iron or cobalt catalyst. However, the catalysts and catalyst systems disclosed in these references are described for use in the context of olefin polymerizations and/or oligomerisations, not in the context of hydrosilylation reactions. U.S. Pat. No. 8,236,915 discloses manganese, iron, cobalt or nickel complexes containing terdentate pyridine diimine ligands and their use as efficient and selective hydrosilylation catalysts.

There is a continuing need in the hydrosilation industry for highly 1,2-regioselective hydrosilylation of conjugated 1,3-dienes. The present invention provides one answer to that need.

SUMMARY OF THE INVENTION

In one aspect, the present invention is directed to a process for the hydrosilylation of a compound containing a terminally unsaturated 1,3-diene, the process comprising (i) contacting a composition containing a silyl hydride and a compound containing a terminally unsaturated 1,3-diene with a complex of Formula (Ia) or (Ib), optionally in the presence of a solvent, to cause the silyl hydride to react with the compound containing a terminally unsaturated 1,3-diene to produce a 1,2-hydrosilylation product containing said complex, and (ii) optionally removing the complex from the 1,2 hydrosilylation product; wherein the compound containing a terminally unsaturated 1,3-diene has the formula $CH_2=CH-CR=CHR'$ where R and R' are independently a saturated or unsaturated alkyl or aryl group or a halogen radical, with the proviso that R' is H for isoprene and chloroprene; and wherein the complex of Formula (Ia) or (Ib) is

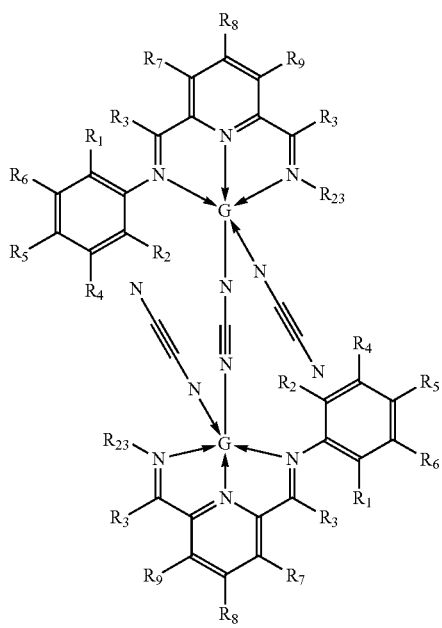

(Ia)

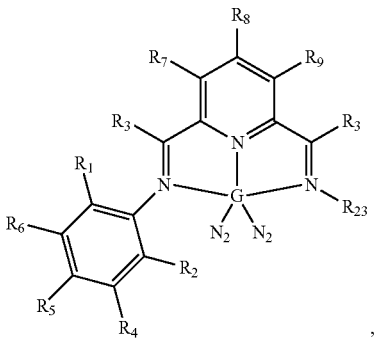

(Ib)

wherein:
G is Fe;
each occurrence of $R_1$, $R_2$, $R_3$, $R_4$, $R_5$, $R_6$, $R_7$, $R_8$, and $R_9$ is independently hydrogen, C1-18 alkyl, C1-C17 substituted alkyl, aryl, substituted aryl, wherein $R_2$-$R_9$, other than hydrogen, optionally contain at least one heteroatom;
each occurrence of $R_{23}$ is independently C1-C18 alkyl, C1-C18 substituted alkyl, aryl or substituted aryl, wherein $R_{23}$ optionally contains at least one heteroatom;
optionally any two neighboring $R_1$, $R_2$, $R_3$, $R_4$, $R_5$, $R_6$, $R_7$, $R_8$, $R_9$, and $R_{23}$ groups taken together may form a ring being a substituted or unsubstituted, saturated, or unsaturated cyclic structure.

In another aspect, the present invention is directed to a 1,2-hydrosilylation product produced by the above process, wherein the compound containing the terminally unsaturated 1,3-diene is isoprene, 1,3-hexadiene, myrcene, or chloroprene, and wherein the product is low in or essentially free of the 1,4-hydrosilylation product. In one embodiment, the product has about 10 mol % or less; about 5 mol % or less; even about 1 mol % or less of the 1,4-adduct.

DETAILED DESCRIPTION OF THE INVENTION

As used herein, "alkyl" includes straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "unsaturated" is meant one or more double or triple bonds. In one embodiment, it refers to carbon-carbon double bonds or triple bonds.

Any hetero-atom-containing group, if present, is inert under the hydrosilylation process conditions to which the compound containing the group is subjected. Examples of such groups include halo (fluoro, chloro, bromo, and iodo), ether such as —$OR^{30}$ wherein $R^{30}$ is hydrocarbyl or substituted hydrocarbyl.

"Heteroatoms" as used herein means any of the Group 13-17 elements except carbon, and can include, but is not limited to, for example, oxygen, nitrogen, silicon, sulfur, phosphorus, fluorine, chlorine, bromine, and iodine.

As indicated above, the present invention is directed to a process for the hydrosilylation of conjugated dienes, and particularly compounds containing a terminally unsaturated 1,3-diene. The inventors have discovered that a class of iron pyridine diimine complexes is capable of selectively producing 1,2-addition products in a hydrosilylation reaction between a silyl hydride and a terminally unsaturated 1,3-diene. The 1,2-addition products that are produced by the process of the present invention have uses in the synthesis of new silicone materials such as silanes, silicone fluids, and crosslinked silicone elastomers. These materials, in turn, can be used in applications such as coatings, for example release coatings, room temperature vulcanizates, sealants, adhesives, products for agricultural and personal care applications, and silicone surfactants for stabilizing polyurethane foams.

The process of the invention comprises the steps of (i) contacting a composition containing a silyl hydride and a compound containing a terminally unsaturated 1,3-diene with a catalyst complex of Formula (Ia) or (Ib), optionally in the presence of a solvent, to cause the silyl hydride to react with the compound containing a terminally unsaturated 1,3-diene to produce a 1,2-hydrosilylation product containing the complex. The process of the invention also includes the optional step of removing the complex from the 1,2-hydrosilylation product. In one embodiment, the compound containing a terminally unsaturated 1,3-diene has the formula $CH_2$=CH—CR=CHR' where R and R' independently are a saturated or unsaturated alkyl or aryl group or a halogen radical, with the proviso that R' is H for isoprene and chloroprene.

The complex of Formula (Ia) has the structure

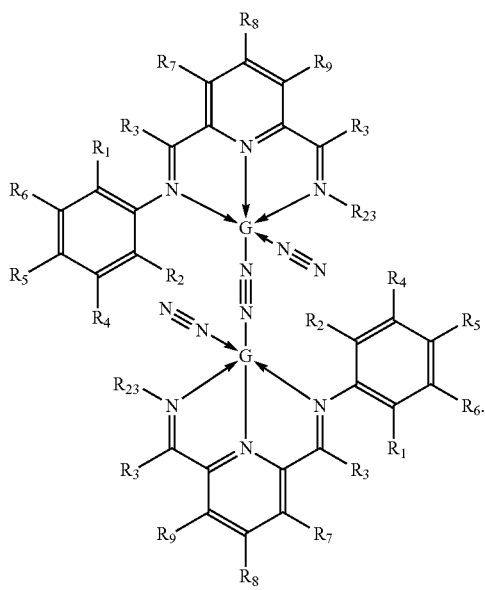

The complex of Formula (Ib) is the monomeric counterpart to Formula (Ia), and has the structure

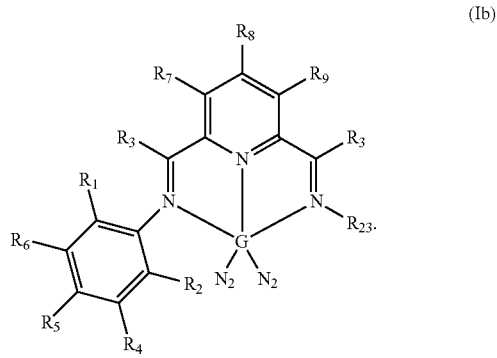

In both Formula (Ia) and (Ib), G is Fe; each occurrence of $R_1$, $R_2$, $R_3$, $R_4$, $R_5$, $R_6$, $R_7$, $R_8$, and $R_9$ is independently hydrogen, C1-18 alkyl, C1-C18 substituted alkyl, aryl, substituted aryl, or an inert substituent, wherein $R_2$-$R_9$, other than hydrogen, optionally contain at least one heteroatom;

each occurrence of $R_{23}$ is independently C1-C18 alkyl, C1-C18 substituted alkyl, aryl or substituted aryl, wherein $R_{23}$ optionally contains at least one heteroatom;

optionally any two neighboring $R_1$, $R_2$, $R_3$, $R_4$, $R_5$, $R_6$, $R_7$, $R_8$, $R_9$, and $R_{23}$ groups taken together may form a ring being a substituted or unsubstituted, saturated, or unsaturated cyclic structure.

In some embodiments, the complexes of Formulas (Ia) and (Ib) have the following substituents: (1) $R_{23}$ is

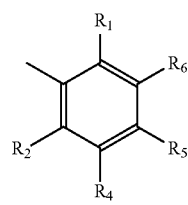

and/or (2) $R_1$ is hydrogen, methyl, ethyl, n-propyl or isopropyl; and/or (3) $R_1$ and $R_2$ are both methyl, ethyl, n-propyl or isopropyl groups; and/or (4) $R_3$ is methyl; and/or (5) $R_4$-$R_9$ are hydrogen; and/or (6) $R_{10}$, $R_{11}$, $R_{13}$, $R_{14}$, $R_{15}$, and $R_{16}$ are hydrogen; and/or (7) $R_{22}$ is —$CH_2SiR^{20}_3$, wherein each occurrence of $R^{20}$ is C1-C18 alkyl, C1-C18 substituted alkyl, aryl or substituted aryl, preferably $R^{20}$ is a methyl group. In one preferred embodiment, Formula (Ia) is [($^{Me}$PDI)FeN$_2$]$_2$($\mu_2$-N$_2$). In another preferred embodiment, Formula (Ib) is ($^{Me}$PDI)Fe(N$_2$)$_2$. In the various embodiments, the $^{Me}$PDI moiety in the formulas refers to N,N'-bis (2,6-xylyl)pyridine-2,6-diimine, with each imine nitrogen bearing a 2,6-xylyl substituent.

Various methods can be used to prepare complexes of Formulas (Ia) and (Ib). One preferred method is disclosed in U.S. Pat. No. 8,236,915, herein incorporated by reference in its entirety. This method includes the step of activating a compound of Formula (II) with a reducing agent in the presence of nitrogen, wherein Formula (II) is

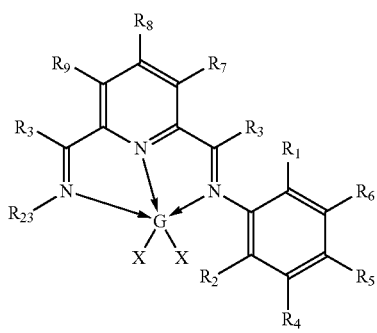

Formula (II)

wherein G is Fe;

each occurrence of $R_1$, $R_2$, $R_3$, $R_4$, $R_5$, $R_6$, $R_7$, $R_8$, and $R_9$ is independently H, C1-18 alkyl, C1-C18 substituted alkyl, aryl, substituted aryl, or an inert group, wherein $R_2$-$R_9$, other than hydrogen, optionally contain at least one heteroatom;

$R_{23}$ is C1-C18 alkyl group or C1-C18 substituted alkyl, aryl or substituted aryl group, wherein $R_{23}$ optionally contains at least one heteroatom;

optionally any two neighboring $R_1$, $R_2$, $R_3$, $R_4$, $R_5$, $R_6$, $R_7$, $R_8$, $R_9$, and $R_{23}$ groups taken together may form a ring being a substituted or unsubstituted, saturated, or unsaturated cyclic structure, X is an anion, preferably F, Cl, Br, I, $CF_3R^{40}SO_3^-$ or $R^{50}COO^-$, wherein $R^{40}$ is a covalent bond or a C1-C6 alkylene group, and $R^{50}$ is a C1-C10 substituted or unsubstituted hydrocarbyl group.

Preferably, the reducing agent has a reduction potential more negative than −0.6 v (versus ferrocene, as described in Chem. Rev. 1996, 96, 877-910. A larger negative number represents a larger reduction potential). The most preferred reducing agents have a reduction potential in the range of −2.8 to −3.1 v. An exemplary reducing agent includes, but is not limited to, sodium naphthalenide.

The methods to prepare the compounds represented by structural Formula (II) are known to a person skilled in the field. For example, the compounds of Formula (II) can be prepared from a PDI ligand and a metal halide, such as $FeBr_2$. Typically, the PDI ligands are produced through condensation of an appropriate amine or aniline with 2,6-diacetylpyridine and its derivatives. If desired, the PDI ligands can be further modified by known aromatic substitution chemistry.

When used as catalysts for the hydrosilylation reactions, the complexes of Formulas (Ia) and (Ib) can be unsupported or immobilized on a support material, for example, carbon, silica, alumina, $MgCl_2$ or zirconia, or on a polymer or prepolymer, for example polyethylene, polypropylene, polystyrene, or poly(aminostyrene). The metal complexes can also be supported on dendrimers.

In some embodiments, for the purposes of attaching the metal complexes of the invention to a support, it is desirable that at least one of $R_1$ to $R_9$ of the metal complexes, preferably $R_6$, has a functional group that is effective to covalently bond to the support. Exemplary functional groups include but are not limited to SH, COOH, $NH_2$ or OH groups.

In one embodiment, silica supported catalyst may be prepared via Ring-Opening Metathesis Polymerization (ROMP) technology as discussed in the literature, for example Macromol. Chem. Phys. 2001, 202, No. 5, pages 645-653; Journal of Chromatography A, 1025 (2003) 65-71.0

One way to immobilize catalysts on the surface of dendrimers is by the reaction of Si—Cl bonded parent dendrimers and functionalized PDI in the presence of a base is as illustrated by Kim et al. in Journal of Organometallic Chemistry 673 (2003) 77-83.

In one embodiment, the complexes of Formula (Ia) and (Ib) are used as catalysts for the hydrosilylation of a composition containing a silyl hydride and a compound having a terminally unsaturated 1,3-diene with the structure $CH_2$=CH—CR=CHR' where R and R' independently is a saturated or unsaturated alkyl or aryl group or a halogen radical, with the proviso that R' is H for isoprene and chloroprene.

The process includes contacting the composition with a metal complex of Formula (Ia) or (Ib), either supported or unsupported, to cause the silyl hydride to react with the compound having a terminally unsaturated 1,3-diene to produce a hydrosilylation product which may contain the metal complex catalyst. The hydrosilylation reaction can be conducted optionally in the presence of a solvent. If desired, when the hydrosilylation reaction is completed, the metal complex can be removed from the reaction product by magnetic separation and/or filtration.

The silyl hydride employed in the hydrosilylation reaction is not particularly limited. It can be any compound selected from the group consisting of $R_aSiH_{4-a}$, $(RO)_aSiH_{4-a}$, $Q_uT_vT_p^HD_wD^H_xM^H_yM_z$, and combinations thereof. The silyl hydride can contain linear, branched or cyclic structures, or combinations thereof. As used herein, each occurrence of R is independently C1-C18 alkyl, C1-C18 substituted alkyl, wherein R optionally contains at least one heteroatom, each occurrence of a independently has a value from 1 to 3, each of p, u, v, y and z independently has a value from 0 to 20, w and x are from 0 to 500, provided that p+x+y equals 1 to 500 and the valences of the all the elements in the silyl hydride are satisfied. Preferably, p, u, v, y, and z are from 0 to 10, w and x are from 0 to 100, wherein p+x+y equals 1 to 100.

As used herein, an "M" group represents a monofunctional group of formula $R'_3SiO_{1/2}$, a "D" group represents a difunctional group of formula $R'_2SiO_{1/2}$, a "T" group represents a trifunctional group of formula $R'SiO_{3/2}$, and a "Q" group represents a tetrafunctional group of formula $SiO_{4/2}$, an "$M^H$" group represents $HR'_2SiO_{1/2}$ a "$T^H$" represents $HSiO_{3/2}$, and a "$D^H$" group represents $R'HSiO_{2/2}$. Each occurrence of R' is independently C1-C18 alkyl, C1-C18 substituted alkyl, wherein R' optionally contains at least one heteroatom. In one preferred embodiment, the silyl hydride has the structure $MD^HM$.

The compound containing a terminally unsaturated 1,3-diene has the structure $CH_2$=CH—CR=CHR' where R and R' independently is a saturated or unsaturated alkyl or aryl group or halogen radical, with the proviso that R' is H for isoprene and chloroprene. Examples of such structures include, but are not limited to, isoprene, 1,3-hexadiene, myrcene, chloroprene and the like.

The catalyst loading and reaction time can be selected as desired. In one embodiment, the catalyst loading is from about 0.05 mol % to about 5 mol %; from about 0.1 mol % to about 2.5 mol %; even from about 0.2 mol % to about 1 mol %. In one embodiment the catalyst loading is from about 0.1 mol % to about 0.25 mol %. Here as elsewhere in the specification and claims, numerical values can be used to form new and non-disclosed or non-specified ranges. As used herein the mol % of catalyst refers to the moles of catalyst in relation to the total moles of substrate. The mol % of catalyst can be calculated as: $(mol_{Catalyst}/(mol_{silane}+mol_{olefin}))\times 100$.

In one embodiment, the reactions can be conducted for a period of from about 1 hour to about 24 hours; from about 5 hours to about 20 hours; even from about 10 hours to about 15 hours. Here as elsewhere in the specification and claims, numerical values can be used to form new and non-disclosed or non-specified ranges. The reaction can be conducted, in one embodiment, at room temperature (from about 23° C. to about 30° C.).

The process of the invention is efficient and selective in producing the 1,2-addition product in hydrosilylation reactions with 1,3-conjugated dienes. When an appropriate silyl hydride, for example, $MD^HM$, is reacted with a 1,3-conjugated diene such as isoprene or myrcene in the presence of the iron catalyst, the resulting product is the 1,2-addition product. The reaction is essentially free of internal addition products and isomerization products of the reactants. As used herein, "essentially free" is meant no more than 10 wt %, preferably 5 wt % based on the total weight of the 1,2-product. "Essentially free of internal addition products" is meant that silicon is added to the terminal carbon. Further, in one embodiment, the product is low in or essentially free of the 1,4-hydrosilylation product. In one embodiment, the product has about 10 mol % or less; about 5 mol % or less; even about 1 mol % or less of the 1,4-adduct. As used herein, "essentially free of 1,4-hydrosilylation product" is meant no more than 10 mol %; no more than 5 mol %; even no more than 1 mol % of 1,4-hydrosilylation product.

Since the 1,2-adducts of the process of the present invention retain a reactive C=C unsaturation, they are readily amenable to further chemistry, including hydrosilylation or peroxide initiated cross-linking to generate useful materials such as elastomers. They can also be used as comonomers together with many organic monomers to generate silyl-functional polyenes in the polyolefin industry. The resulting polyolefin can be enabled with moisture curing functionality, for example.

The following examples are intended to illustrate, but in no way limit the scope of the present invention. All parts and percentages are by weight and all temperatures are in degrees Celsius unless explicitly stated otherwise. All the publications and the US patents referred to in the application are hereby incorporated by reference in their entireties.

EXAMPLES

General Considerations

All air- and moisture-sensitive manipulations were carried out using standard vacuum line, Schlenk, and cannula techniques or in an MBraun inert atmosphere drybox containing an atmosphere of purified nitrogen. Solvents for air- and moisture-sensitive manipulations were initially dried and deoxygenated using literature procedures. See for example Pangborn et al., J. Organometallics 1996, 15, 1518.

The following abbreviations and terms are used:
bs—broad singlet
s—singlet
t—triplet
bm—broad multiplet
GC—Gas Chromatography
MS—Mass Spectroscopy
THF—tetrahydrofuran Example 1: Hydrosilylation of Isoprene A thick-walled glass vessel was charged with 0.100 g (0.449 mmol) of $MD^HM$ and 0.002 g (0.002 mmol, 0.2 mol %) of $[(^{Me}PDI)FeN_2]_2(\mu_2-N_2)$. The solution was frozen by submerging the vessel in liquid nitrogen and then degassed. 0.449 mmol (P=83 torr, T=297 K, V=0.1001 L) of isoprene was admitted using a calibrated gas bulb. The solution was thawed and warmed to room temperature and stirred for one hour. Analysis of the product mixture by GC and NMR spectroscopy established quantitative conversion of the substrates to 4-(TMSO)$_2$MeSi-2-methyl-1-butene:

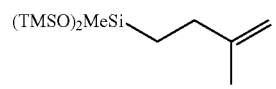

$^1$H NMR (500 MHz, CDCl$_3$): δ=0.03 (s, 3H, (OTMS)$_2$SiCH$_3$), 0.10 (s, 18H, OSi(CH$_3$)$_3$), 0.61 (t, 2H, C$^4$H$_2$), 1.73 (s, 3H, C$^2$CH$_3$), 2.01 (t, 2H, C$^3$H$_2$), 4.67 (s, 1H, C$^1$H), 4.70 (s, 1H, C1H). {$^1$H} $^{13}$C NMR (125 MHz, CDCl$_3$): δ=−0.22 ((OTMS)$_2$SiCH$_3$), 2.01 (OSi(CH$_3$)$_3$), 15.99 (C$^4$), 22.34 (C$^2$CH$_3$), 31.27 (C$^3$), 108.48 (C$^1$), 148.55 (C$^2$).

Example 2: Hydrosilylation of Myrcene

A scintillation vial was charged with 0.120 g (0.881 mmol) of myrcene and 0.200 g (0.899 mmol, 1.02 equiv of $MD^HM$. The precatalyst 0.004 g (0.004 mmol, 0.2 mol %) of $[(^{Me}PDI)Fe(N_2)]_2(\mu_2-N_2)$ was then added to the vial, and the reaction was stirred at room temperature. The reaction was stirred for 1 hour at room temperature and quenched by exposure to air. Analysis of the product mixture by GC and NMR spectroscopy established quantitative conversion of the olefin to 1-(TMSO)$_2$MeSi-3-methylene-7-methyloct-6-ene.

$^1$H NMR (500 MHz, CDCl$_3$): δ=0.03 (s, 3H, (OTMS)$_2$SiCH$_3$), 0.10 (s, 18H, OSi(CH$_3$)$_3$), 0.61 (m, 2H, C$^1$H$_2$), 1.62 (s, 3H, C$^8$H$_3$), 1.70 (s, 3H, C$^7$HCH$_3$), 2.02 (m, 2H, C$^2$H$_2$), 2.05 (m, 2H, C$^4$H$_2$), 2.11 (m, 2H, C$^5$H$_2$), 4.69 (s, 1H, C$^3$CH), 4.75 (s, 1H, C$^3$CH), 5.13 (m, 1H, C$^6$H). {$^1$H} $^{13}$C NMR (125 MHz, CDCl$_3$): δ=−0.21 ((OTMS)$_2$SiCH$_3$), 2.01 (OSi(CH$_3$)$_3$), 15.97 (C$^1$), 17.82 (C$^8$), 25.88 (C$^7$CH$_3$), 26.66 (C$^5$), 29.57 (C$^2$), 35.99 (C$^4$), 107.59 (C$^3$CH$_2$), 124.40 (C$^6$), 131.64 (C$^7$), 152.28 (C$^3$).

Example 3: Hydrosilylation of 1,3-hexadiene

A scintillation vial was charged with 0.082 g (1 mmol) of 1,3-hexadiene and 0.223 g (1 mmol, 1 equiv) of $MD^HM$. The precatalyst 0.004 g (0.005 mmol, 0.25 mol %) of $[(^{Me}PDI)Fe(N_2)]_2(\mu_2-N_2)$ was then added to the vial, and the reaction was stirred at room temperature. The reaction was stirred for 24 hour at room temperature and quenched by exposure to air. Analysis of the product mixture by GC and NMR spectroscopy established 70% conversion of the silane to 1-(TMSO)$_2$MeSi-3-hexene.

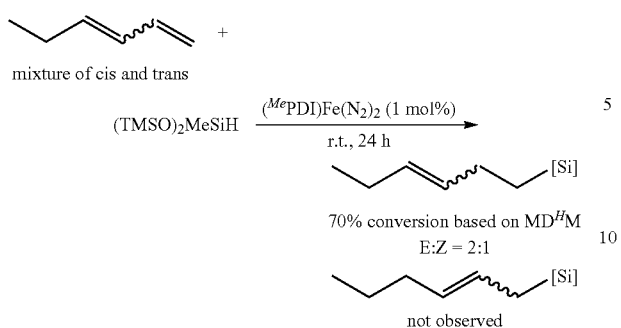

$^1$H NMR (500 MHz, CDCl$_3$): δ=0.03 (s, 3H, (OTMS)$_2$SiCH$_3$), 0.10 (s, 18H, OSi(CH$_3$)$_3$), 0.49-0.38 (m, 2H, C$^1$H$_2$), 0.96-0.82 (m, 3H, C$^6$H$_3$), 2.07-1.85 (m, 4H, C$^{2,5}$H$_2$), 5.48-5.09 (m, 4H, C$^{3,4}$H). {$^1$H} $^{13}$C NMR (125 MHz, CDCl$_3$): δ=132.23 (C$^4$ (E)), 132.02 (C$^4$ (Z)), 130.52 (C$^3$ (Z)), 130.27 (C$^3$ (E)), 26.19 (C$^5$ (E)), 25.68 (C$^5$ (Z)), 20.76 (C$^2$ (E)), 20.52 (C$^2$ (Z)), 18.27 (C$^1$ (E)), 17.74 (C$^1$ (Z)), 14.56 (C$^6$ (Z)), 14.13 (C$^6$ (Z)), 2.02 (OSi(CH$_3$)$_3$), 1.83 (SiCH$_3$).

Example 4: Dihydrosilylation of Myrcene

This reaction was performed in a manner similar to the hydrosilylation of myrcene using 0.120 g (0.881 mmol) of myrcene, 0.400 g (1.80 mmol, 2.04 equiv) of MD$^H$M and 0.004 g (0.004 mmol, 0.1 mol %) of [($^{Me}$PDI)Fe(N$_2$)]$_2$(μ$_2$-N$_2$). The reaction was stirred for 24 hours at room temperature and quenched by exposure to air. Analysis of the product mixture by GC and NMR spectroscopy established complete conversion of the olefin to 1-(TMSO)$_2$MeSi-3-((TMSO)$_2$MeSi)methyl-7-methyl-oct-6-ene:

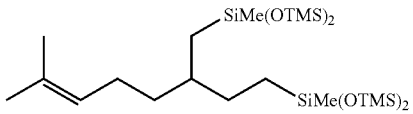

$^1$H NMR (500 MHz, CDCl$_3$): δ=0.02 (s, 3H, (OTMS)$_2$SiCH$_3$), 0.04 (s, 3H, (OTMS)$_2$SiCH$_3$), 0.11 (s, 36H, OSi(CH$_3$)$_3$), 0.41 (t, 2H, C$^3$CH$_2$), 0.49 (dd, 2H, C$^1$H$_2$), 1.30 (m, 2H, C$^2$H$_2$), 1.32 (m, 2H, C$^4$H$_2$), 1.50 (m, 1H, CH), 1.62 (s, 3H, C$^8$H$_3$), 1.70 (s, 3H, C$^7$CH$_3$), 1.96 (m, 2H, C$^5$H$_2$), 5.13 (t, 1H, C$^6$H$_2$). {$^1$H} $^{13}$C NMR (125 MHz, CDCl$_3$): δ=−0.17 ((OTMS)$_2$SiCH$_3$), 1.23 ((OTMS)$_2$SiCH$_3$), 2.09 (OSi(CH$_3$)$_3$), 13.92 (C$^3$CH$_2$), 17.84 (C$^8$), 22.58 (d), 25.93 (C$^7$CH$_3$), 25.44 (C$^5$), 29.24 (C$^2$), 35.46 (C$^3$), 35.84 (C$^4$), 125.38 (C$^6$), 130.92 (C$^7$).

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for the hydrosilylation of a compound containing a terminally unsaturated 1,3-diene, the process comprising (i) contacting a composition containing a silyl hydride and a compound containing a terminally unsaturated 1,3-diene with a complex of Formula (Ia) or (Ib), optionally in the presence of a solvent, to cause the silyl hydride to react with the compound containing a terminally unsaturated 1,3-diene to produce selectively a 1,2-hydrosilylation product containing said complex, and (ii) optionally removing the complex from the 1,2-hydrosilylation product;

wherein the compound containing a terminally unsaturated 1,3-diene has the formula CH$_2$=CH—CR=CHR' where R and R' independently is a saturated or unsaturated alkyl or aryl group or a halogen radical, with the proviso that R' is H for isoprene and chloroprene; and wherein the complexes of Formula (Ia) and (Ib) are

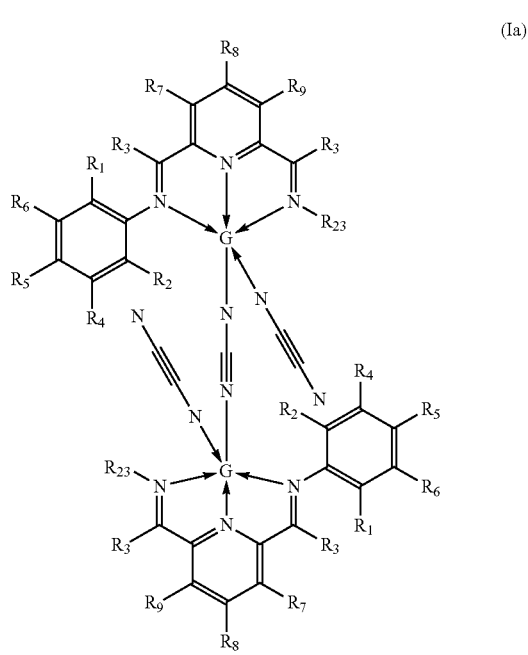

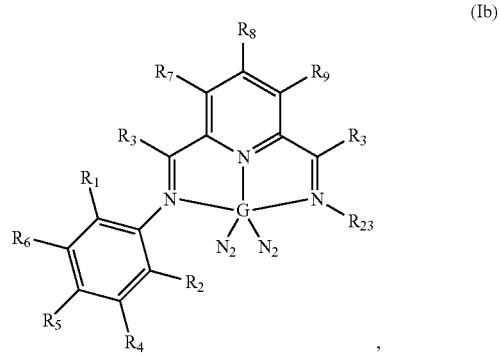

wherein:
G is Fe;
each occurrence of R$_1$, R$_2$, R$_3$, R$_4$, R$_5$, R$_6$, R$_7$, R$_8$, and R$_9$ is independently hydrogen, C1-18 alkyl, C1-C18 substituted alkyl, aryl, substituted aryl, or an inert substituent, wherein R$_2$-R$_9$, other than hydrogen, optionally contain at least one heteroatom;
each occurrence of R$_{23}$ is independently C1-C18 alkyl, C1-C18 substituted alkyl, aryl or substituted aryl, wherein R$_{23}$ optionally contains at least one heteroatom;
optionally any two neighboring R$_1$, R$_2$, R$_3$, R$_4$, R$_5$, R$_6$, R$_7$, R$_8$, R$_9$, and R$_{23}$ groups taken together may form a ring being a substituted or unsubstituted, saturated, or unsaturated cyclic structure.

2. The process of claim 1, wherein $R_{23}$ is

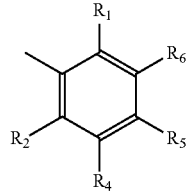

wherein $R_1$, $R_2$, $R_4$, $R_5$ and $R_6$ are as defined in claim 1.

3. The process of claim 1, wherein $R_1$ and $R_2$ are both methyl, ethyl, propyl or isopropyl groups.

4. The process of claim 1, wherein $R_3$ is methyl.

5. The process of claim 1, wherein $R_1$ and $R_2$ are both methyl, $R_4$, $R_5$, and $R_6$ are hydrogen, and $R_{23}$ is 2,6-xylyl.

6. The process of claim 1, wherein the complex of Formula (Ia) is $[(^{Me}PDI)FeN_2]_2(\mu_2\text{-}N_2)$ or the complex of Formula (Ib) is $(^{Me}PDI)Fe(N_2)_2$.

7. The process of claim 1, wherein the complex is immobilized on a support.

8. The process of claim 7, wherein the support is selected from the group consisting of carbon, silica, alumina, $MgCl_2$, zirconia, polyethylene, polypropylene, polystyrene, poly(aminostyrene), dendrimers, and combinations thereof.

9. The process of claim 7, wherein at least one of $R_1$-$R_9$ contains a functional group that covalently bonds with the support.

10. The process of claim 1, further comprising the step of removing the complex from the hydrosilylation product by magnetic separation and/or filtration.

11. The process of claim 1, wherein the silyl hydride is selected from the group consisting of $R_aSiH_{4-a}$, $(RO)_aSiH_{4-a}$, $Q_uT_vT_p^HD_wD_x^HM_y^HM_z$, and combinations thereof, wherein Q is $SiO_{4/2}$, T is $R'SiO_{3/2}$, $T^H$ is $HSiO_{3/2}$, D is $R'_2SiO_{2/2}$ $D^H$ is $R'HSiO_{2/2}$, $M^H$ is $HR'_2SiO_{1/2}$, M is $R'_3SiO_{1/2}$, each occurrence of R and R' is independently C1-C18 alkyl, C1-C18 substituted alkyl, wherein R and R' optionally contain at least one heteroatom, each occurrence of a independently has a value of from 1 to 3, g has a value of from 0 to 3, each of p, u, v, y and z is independently from 0 to 20, w and x are independently from 0 to 500, provided that p+x+y equals 1 to 500, and the valences of the all the elements in the silyl hydride are satisfied.

12. The process of claim 11, wherein each of p, u, v, y, and z is independently from 0 to 10, w and x are independently from 0 to 100, wherein p+x+y equals 1 to 100.

13. The process of claim 1, wherein the silyl hydride is $MD^HM$.

14. The process of claim 1, wherein the compound containing the terminally unsaturated 1,3-diene is isoprene, 1,3-hexadiene, myrcene, or chloroprene.

15. The process of claim 1, wherein the catalyst is present in an amount of from about 0.05 mol % to about 5 mol %.

16. The process of claim 1, wherein the catalyst is present in an amount of about 0.25 mol %.

17. The process of claim 1, wherein the reaction is conducted over a period of from about 1 hour to about 24 hours.

18. The process of claim 1, wherein the reaction is conducted over a period of about 24 hours.

19. A 1,2-hydrosilylation product produced from the process of claim 1, wherein the compound containing the terminally unsaturated 1,3-diene is isoprene, 1,3-hexadiene, myrcene, or chloroprene, and wherein the product comprises (i) about 5 mol % or less of a 1,4-hydrosilylation product, an internal adduct, and/or an isomerization by-product, and (ii) the complex of (Ia) or (Ib).

* * * * *